(12) United States Patent
Bender et al.

(10) Patent No.: US 8,755,587 B2
(45) Date of Patent: Jun. 17, 2014

(54) METHOD FOR PROVIDING A 3D IMAGE DATA RECORD OF A PHYSIOLOGICAL OBJECT WITH A METAL OBJECT THEREIN

(75) Inventors: Frederik Bender, Erlangen (DE); Kevin Royalty, Fitchburg, WI (US)

(73) Assignee: Siemens Aktiengesellschaft, Munich (DE)

( * ) Notice: Subject to any disclaimer, the term of this patent is extended or adjusted under 35 U.S.C. 154(b) by 162 days.

(21) Appl. No.: 13/407,793

(22) Filed: Feb. 29, 2012

(65) Prior Publication Data

US 2012/0224761 A1 Sep. 6, 2012

(30) Foreign Application Priority Data

Mar. 4, 2011 (DE) .......................... 10 2011 005 119

(51) Int. Cl.
*G06K 9/00* (2006.01)
(52) U.S. Cl.
USPC .......................................................... 382/132
(58) Field of Classification Search
USPC ................. 345/653, 664, 679; 378/68, 98.12;
382/132; 430/967; 604/20; 700/59;
702/152, 153; 715/782, 848, 850
See application file for complete search history.

(56) References Cited

U.S. PATENT DOCUMENTS

| | | | |
|---|---|---|---|
| 5,396,418 A | 3/1995 | Heuscher | |
| 5,841,830 A | 11/1998 | Barni | |
| 7,568,837 B2 * | 8/2009 | Heigl et al. | 378/207 |
| 2006/0285638 A1 | 12/2006 | Boese et al. | |
| 2008/0181367 A1 * | 7/2008 | Heigl et al. | 378/207 |
| 2009/0180589 A1 * | 7/2009 | Wang et al. | 378/65 |

FOREIGN PATENT DOCUMENTS

| | | |
|---|---|---|
| DE | 102005028746 A1 | 12/2006 |
| DE | 102008006516 A1 | 8/2009 |
| JP | 005324883 B2 * | 10/2008 |

* cited by examiner

*Primary Examiner* — Gregory F Cunningham

(57) ABSTRACT

A method for providing a 3D image data record of a physiological object with a metal object therein is proposed. To enable an image of the metal object in the physiological object, for instance a biopsy needle in a human patient to be recorded as a 3D image in this patient, two 2D x-ray images of the patient are obtained with the needle with the aid of a biplane x-ray system, and back projection allows a 3D image data record to be generated, which is then subject to a filtering with a gray-scale value window. After filtering, information relating to the position and shape of the metal object in space is obtained. The thus obtained first 3D image data record can be combined with another 3D image data record, in particular with a 3D image data record of the patient without the metal object obtained with the same biplane x-ray system.

9 Claims, 1 Drawing Sheet

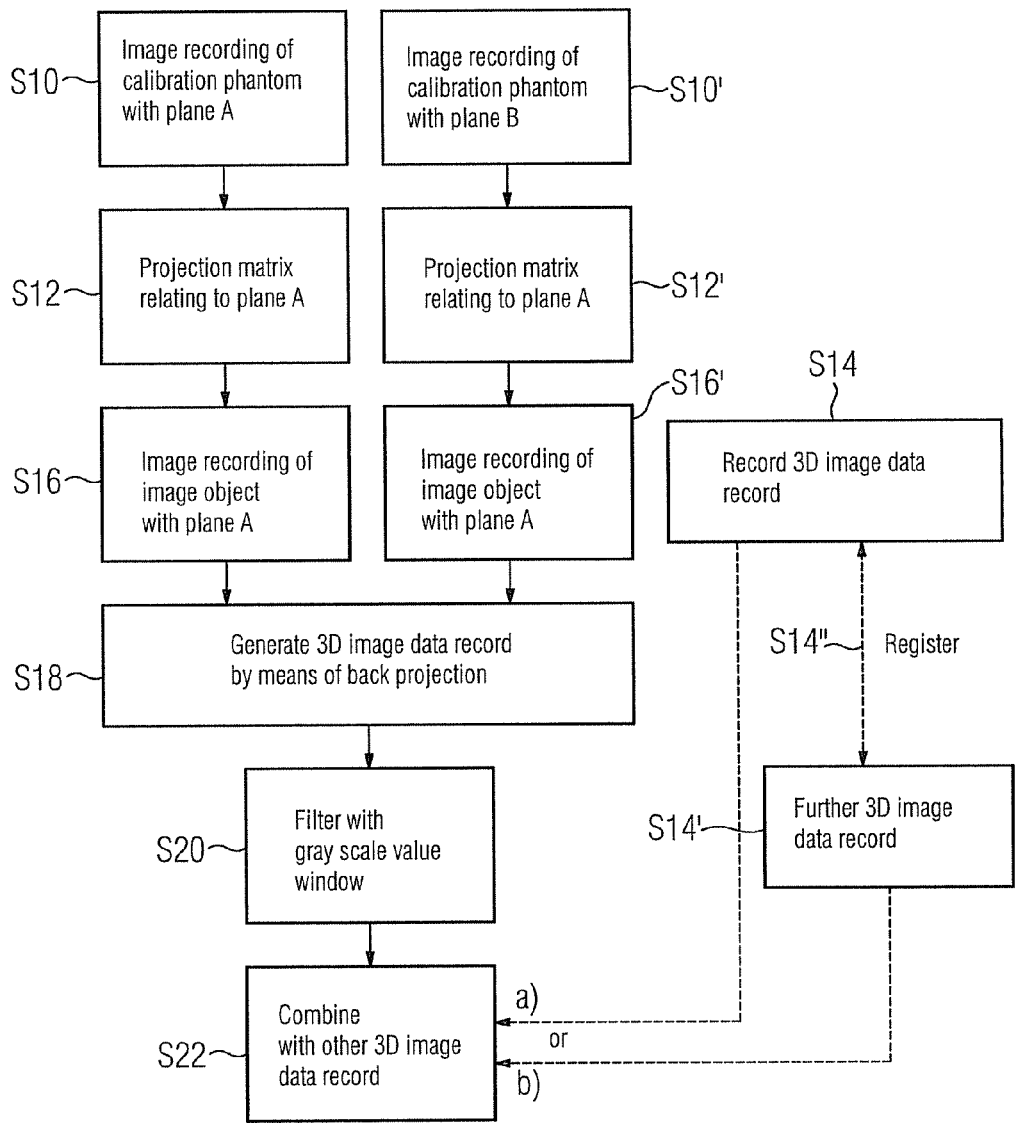

METHOD FOR PROVIDING A 3D IMAGE DATA RECORD OF A PHYSIOLOGICAL OBJECT WITH A METAL OBJECT THEREIN

CROSS REFERENCE TO RELATED APPLICATIONS

This application claims priority of German application No. 10 2011 005 119.8 filed Mar. 4, 2011, which is incorporated by reference herein in its entirety.

FIELD OF INVENTION

The invention relates to a method for providing a 3D image data record for the purpose of recording an image of a physiological object with a metal object located therein. The physiological object may in particular be a patient and the metal object may be an object or part of an object, which is inserted into the patient within the scope of a medical treatment. The metal object may therefore include a needle inserted into the body of the patient, or also a guidewire.

BACKGROUND OF INVENTION

Thus for instance, during the biopsy of a tumor, a hollow needle is pushed into the patient in order to take tissue samples of the tumor which can then be analyzed later in a lab. It must be ensured here that the removed sample is part of the non-necrotic tumor mass. The needle must therefore be pushed into the tumor very precisely. A type of needle navigation is therefore needed. The navigation takes place under the supervision of the physician, who observes images of the needle located in the tissue and refers thereto during insertion thereof. Automatic modes of navigation are also conceivable.

The said method for tumor biopsy applies equally to other methods in which a needle is inserted into the patient body, for instance to the so-called vertebroplasty, in which bone cement is introduced into a broken bone, in particular a vertebra.

Previously during the intervention, fluoroscopic images of the needle were overlayed with images taken prior to the intervention. Since only one representation of the needle from one single perspective was previously available, at best two with biplane x-ray systems, the positioning of the needle with the aid of images is not easy for the treating physician.

SUMMARY OF INVENTION

It is the object of the present invention to propose a method for providing a 3D image data record for the purpose of recording an image of a physiological object having a metal object located therein, which enables a navigation of a needle by a treating physician (or also automatically) to an improved degree.

The object is achieved by a method having the features according to the claims.

In accordance with the invention, at least two two-dimensional x-ray images of the physiological object having the metal object are obtained. A first 3D image data record is obtained from these (at least) two x-ray images by means of back projection, it being possible to update and represent said first 3D image data record in particular in real-time. This first 3D image data record is then subject to a filtering of said type such that only image information relating to the metal object still exists. A second 3D image data record relating to the physiological object is also obtained, and a combined image data record is calculated from the filtered first 3D image data record and the second 3D image data record.

As a result of two or more two-dimensional x-ray images simultaneously representing the metal object in the physiological object, a first 3D image data record can actually be obtained which is subsequently combined with the other image data record. As a result of the filtering taking place, only one item of information relating to the position and shape of the metal object in the space of the physiological object still remains, and the image information relating to the physiological object is provided by means of the second 3D image data record. This separation of the provision of image data relating to the metal object on the one hand and relating to the physiological object on the other hand enables the respective first and second 3D image data records to be optimized and customized and/or already suitably generated in the first place during their recording.

In a preferred embodiment of the invention, the second image data record is obtained by imaging the physiological object without the metal object. In this way, the metal object does not need to be filtered out of the second image data record. The information about the metal object is then exclusively provided by the first 3D image data record.

In a preferred embodiment of the invention, a 3D image data record is used for the purpose of calculating the combined image data record, said 3D image data recording having been obtained with the same x-ray image recording apparatus as the at least two 2D x-ray images. In this way, positions in the x-ray images and/or the first 3D image data record reconstructed therefrom and positions which are defined for the 3D image data record obtained with the same x-ray image recording apparatus correspond to one another perfectly, so that no additional calculation of imaging rules is needed for the fusion.

With one variant of the invention, it is the second image data record itself which is obtained with the same x-ray image recording apparatus as the at least two 2D x-ray images. This is advantageous in that the patient does not have to be subjected to different image recording apparatuses, but instead only has to be positioned in an image recording apparatus once and can then be x-rayed with and without the metal object.

Conversely with a second variant, the second image data record is obtained with an image recording apparatus that differs from the x-ray image recording apparatus with which the at least two 2D x-ray images were recorded. The second 3D image data record is then registered to the 3D image data record obtained with this x-ray image recording apparatus so that an imaging rule is available. Here calculations are only needed to define the positions in the space, but because the same image object was recorded both by the x-ray image recording apparatus and also the other image recording apparatus, a registration, in other words a positionally and dimensionally-correct assignment of the image data to one another by specifying an imaging rule, is readily available.

With a preferred embodiment of the invention, the two x-ray images are obtained using a biplane x-ray system having two x-ray image recording units, each of which includes an x-ray source and an x-ray detector. With the aid of the biplane x-ray system, the two 2D x-ray images can be simultaneously recorded so that the metal object does not actually change its position and/or the patient with the metal object does not change his/her position. As a result, the first 3D image data record can be calculated particularly precisely and in particular shown and updated in real-time. If the fluoroscopic images are recorded at high image rates (for instance 7.5 images per second), the 3D image data record is also updated with this high image data frequency so that the needle can be traced simultaneously.

For two x-ray image recording units, a projection matrix is preferably determined at a predetermined position in each instance on the basis of an x-ray image of a calibration object, the two 2D x-ray images are obtained at the respective predetermined positions and the back projection then also takes place by using these determined projection matrices. The use of a calibration object allows projection matrices to be specified particularly precisely, and if the two 2D projection images are then recorded at the same predetermined positions, these projection matrices are then also valid without restrictions. The projection matrix is as a rule obtained identical to a plurality of predetermined positions with the aid of a respective x-ray image of a calibration object. The plurality nowadays typically includes all approachable positions which are enabled by the x-ray image recording apparatus. The position can in this way be correspondingly changed during the intervention so that there is no restriction to two predetermined positions.

With a preferred embodiment, the x-ray image recording units of the biplane x-ray system are essentially at right angles to one another, which can be defined with the aid of the x-ray detectors, the planes of which, by definition, adopt an angle of 75° to 105° relative to one another in the respective predetermined positions.

To ensure that the filtering of the metal object takes place particularly effectively, certain gray scale value intervals are assigned to the metal object. The filtering then uses in particular a gray scale value window. If this is a rectangular window, only gray scale values from a specific interval are left.

This is based on the knowledge that the metal object can be identified at its strongest attenuation of x-rays, so that it is reflected in gray scale values which can be distinguished from gray scale values which the physiological object itself produces.

BRIEF DESCRIPTION OF THE DRAWINGS

A preferred embodiment of the invention is described in more detail below with reference to the drawing, in which the single FIGURE shows a flowchart to explain a preferred embodiment of the inventive method.

DETAILED DESCRIPTION OF INVENTION

It is currently assumed that a biplane x-ray system exists, i.e. an x-ray image recording apparatus having two x-ray image recording units, each of which includes an x-ray source and an x-ray detector. The tem, "biplane system" means that the one x-ray detector can lie in a plane and the other x-ray detector can lie in another plane at the same time. The one plane is currently referred to as "plane A", the other as "plane B", whereby these planes are preferably to stand precisely at an angle of 90° relative to one another.

A calibration phantom is now initially brought into the biplane x-ray system and an image is recorded, namely in steps S10 and S10' which are to be completed synchronously by means of the two x-ray image recording units. The respective projection matrix relating to the plane and thus to the position of the x-ray detector and also the x-ray source can be calculated in a manner known per se in step S12 and also in step S12' with the aid of the thus obtained images of the calibration phantom. The calibration phantom is now taken from the biplane x-ray system and a patient is brought into the biplane x-ray system as an image object. A 3D x-ray image data record of the patient can now be obtained in a manner known per se in step S14, by the individual x-ray image recording units being successively rotated in angular steps and a thus cited projection being recorded in each instance. The 3D x-ray image data record is obtained by means of back projection. This is also referred to as 3D x-ray angiography.

A metal object, for instance a biopsy needle, is now introduced into the patient, the image object. An image of the image object with plane A is now recorded in Step S16, in other words by means of the first x-ray image recording unit of the biplane x-ray system in the same position, in which the image recording took place in step S10, and a corresponding image recording at the position according to plane B takes place accordingly in step S16. A 3D image data record can now be generated in step S18 from these two image recordings by means of back projection, whereby the projection matrices calculated in steps S12 and S12' are used. This 3D image data record, which shows the metal object in physiological tissue, is now filtered with a gray-scale value window in step S20. Only those gray scale values which are produced by the metal object are allowed to pass. The 3D image data record of the patient without the metal object recorded in step 14 and the filtered 3D image data record of the metal object in the patient is now available without having recorded an image of the tissue of the patient.

In Step S22, these two 3D image data records are now combined with one another, see alternative a).

In a second alternative b), a further 3D image data record of the patient without metal object is obtained in step S14' outside of the biplane x-ray system with another type of image recording apparatus, for instance with the aid of magnetic resonance tomography. In step S14", the further 3D image data record and the 3D x-ray image data record can then be registered with one another, a positionally and dimensionally-correct assignment therefore takes place by specifying an imaging rule from the coordinate system of the one 3D image data record to the other. According to alternative b) in step S22, the combining of the 3D image data record filtered with the gray scale value window in step S20 with the further 3D image data record can now take place. The imaging rule relating to 3D x-ray image data record is precisely the same rule as required for the 3D image data record which was filtered in step S20, because the image recording according to S14 took place with the same biplane x-ray system as the image recording in steps S16 and S16'. (A registration is not necessary with alternative a)).

By means of the invention, metal objects such as in particular needles or also guidewires, possibly in the future even catheters, are provided for the first time in real-time in a three-dimensional representation together with physiological tissue.

The invention claimed is:

1. A method for providing a 3D representation of a physiological object with a metal object located therein, comprising:
   obtaining at least two 2D x-ray images of the physiological object with the metal object by an x-ray image recording apparatus;
   generating a first 3D image data record with the metal object from the at least two x-ray images by back projection;
   filtering the first 3D image data record such that only image information relating to the metal object exists;
   obtaining a second 3D image data record of the physiological object without the metal object;

calculating a combined image data record from the filtered first 3D image data record and the second 3D image data record; and providing a 3D representation of the physiological object with the metal object located therein from the combined image data record.

2. The method as claimed in claim 1, wherein the second 3D image data record is obtained by recording an image of the physiological object without the metal object.

3. The method as claimed in claim 1, wherein a 3D image data record is obtained using the x-ray image recording apparatus for calculating the combined image data record.

4. The method as claimed in claim 3, wherein the second 3D image data record is obtained using the x-ray image recording apparatus.

5. The method as claimed in claim 3, wherein the second image data record is obtained using a different image recording apparatus and is registered to the 3D image data record.

6. The method as claimed in claim 1, wherein the at least two 2D x-ray images are obtained using a biplane x-ray system having two x-ray image recording units each comprising an x-ray source and an x-ray detector respectively.

7. The method as claimed in claim 6, wherein projection matrices are determined based on an x-ray image of a calibration object at predetermined positions, and wherein the at least two 2D x-ray images are obtained at the respective predetermined positions and are back projected using the projection matrices.

8. The method as claimed in claim 6, wherein the two x-ray detectors of the two x-ray image recording units are at an angle between 75° and 105° relative to one another.

9. The method as claimed in claim 1, wherein the first 3D image data record is filtered using a gray scale value window such that only gray scale values which are produced by the metal object are allowed to pass.

* * * * *